United States Patent
Tanabe et al.

(10) Patent No.: US 10,034,855 B2
(45) Date of Patent: Jul. 31, 2018

(54) SOLID COMPOSITION OF PYRROLE CARBOXAMIDE

(71) Applicant: Daiichi Sankyo Company, Limited, Chuo-ku, Tokyo (JP)

(72) Inventors: Hideaki Tanabe, Yokohama (JP); Mina Yamada, Hiratsuke (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/660,625

(22) Filed: Jul. 26, 2017

(65) Prior Publication Data

US 2017/0319544 A1 Nov. 9, 2017

Related U.S. Application Data

(63) Continuation of application No. PCT/JP2016/051956, filed on Jan. 25, 2016.

(30) Foreign Application Priority Data

Jan. 26, 2015 (JP) .................... 2015-012252

(51) Int. Cl.
    *A61K 31/40*     (2006.01)
    *A61K 9/20*     (2006.01)
    *A61K 47/06*     (2006.01)

(52) U.S. Cl.
    CPC ............... *A61K 31/40* (2013.01); *A61K 9/20* (2013.01); *A61K 47/06* (2013.01)

(58) Field of Classification Search
    None
    See application file for complete search history.

(56) References Cited

U.S. PATENT DOCUMENTS 4,693,750 A * 9/1987 Bauer ............... A61K 9/2018
    106/162.9
2008/0234270 A1* 9/2008 Canne Bannen .. C07D 207/416
    514/235.5

FOREIGN PATENT DOCUMENTS

| JP | 2010111657 A | 5/2010 |
| JP | 2014088454 A | 5/2014 |
| JP | 2014162769 A | 9/2014 |
| JP | 2015007116 A | 1/2015 |

OTHER PUBLICATIONS

Nguyen et al. International Journal of Biomedical Science 2006, 85-100.*
Shin-Etsu L-HPC Bulletin 2006.*
Kato, H., et al., Study of the Adaptation of the Standard Formulation to the Direct Compression Method (2)—Effect of Particle Size of Materials, Journal of Pharmaceutical Science and Technology Japan 66(5):370-379, Sep. 2006.
International Search Report dated Mar. 15, 2016, in International Application No. PCT/JP2016/051956, filed Jan. 25, 2016, 10 pages.
DFE Pharma, DFE Pharma no Nyuto Seihin, Seihin Catalog (online), 2013, [retrieval date Feb. 22, 2016], <URL:http://www.dfepharma.jp/ja/jp/downloads.aspx?id=%7BCEOB81DC-9BD8-40BE-8F13-A184F2F2893D%D>, 12 pages (English Translation—p. 4 only).

* cited by examiner

*Primary Examiner* — Jeffrey S Lundgren
*Assistant Examiner* — Michael J Schmitt
(74) *Attorney, Agent, or Firm* — Christensen O'Connor Johnson Kindness PLLC

(57) ABSTRACT

An object is to provide a solid composition of stabilized pyrrole carboxamide. A means for achieving the object is a solid composition for medical use containing (S)-1-(2-hydroxyethyl)-4-methyl-N-[4-(methylsulfonyl)phenyl]-5-[2-(trifluoromethyl)phenyl]-1H-pyrrole-3-carboxamide and an appropriate additive.

18 Claims, No Drawings

SOLID COMPOSITION OF PYRROLE CARBOXAMIDE

CROSS-REFERENCES FOR RELATED APPLICATIONS

This application is a continuation of International Application No. PCT/JP2016/051956, filed Jan. 25, 2016, which claims priority to Japanese Application No. 2015-012252, filed Jan. 26, 2015. Each application is incorporated herein in its entirety.

TECHNICAL FIELD

The present invention relates to a solid composition for medical use in which the storage stability of (S)-1-(2-hydroxyethyl)-4-methyl-N-[4-(methylsulfonyl)phenyl]-5-[2-(trifluoromethyl)phenyl]-1H-pyrrole-3-carboxamide (hereinafter sometimes referred to as "Compound (I)") is high, and a manufacturing method for the solid composition for medical use in which the compound is stabilized.

Further, the present invention relates to a solid product in the form of a tablet, a powder, granules, or a capsule in which Compound (I) is stabilized, and a manufacturing method for such a solid production in the form of a tablet, a powder, granules, or a capsule in which the compound is stabilized.

BACKGROUND ART

Compound (I) represented by the following structural formula:

[Chem. 1]

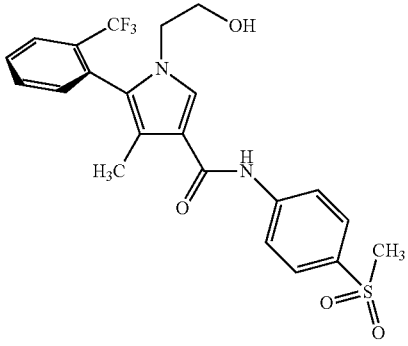

(I)

is disclosed in U.S. Pat. No. 8,524,918, and has an excellent efficacy as a mineralocorticoid receptor (MR) (aldosterone receptor) antagonist, and therefore is expected to have an excellent therapeutic effect and/or preventive effect on a disease such as hypertension, a heart disease [ angina pectoris, myocardial infarction, cardiac arrhythmia (including sudden death), heart failure, or cardiac hypertrophy], a kidney disease (diabetic nephropathy, glomerulonephritis, or nephrosclerosis), a cerebrovascular disease (cerebral infarction or intracranial hemorrhage) or a vascular disorder (arteriosclerosis, restenosis after PTCA, or peripheral circulatory disturbance). Further, an effect on the amelioration of diabetic nephropathy is also expected.

One of the important conditions for the manufacturing of a pharmaceutical product is that the quality (for example, content, tablet hardness, dissolution property, and disintegration property) thereof is maintained from when the product is manufactured to when the product is taken by a patient, for example, in the course of storage in a warehouse, shipping, and storage in a hospital, a pharmacy, or a home, and so on, and high storage stability over a long period of time is required.

CITATION LIST

Patent Literature

PTL 1: WO 2008/126831 (US Patent Application Publication No. 2010-0093826, U.S. Pat. No. 8,524,918)

SUMMARY OF INVENTION

Technical Problem

As a result of intensive studies on a solid composition for medical use of Compound (I) whose storage stability (chemical and/or physical) is enhanced, and a manufacturing method for the solid composition for medical use in which the compound is stabilized, further, a solid product in the form of a tablet, a powder, granules, or a capsule in which Compound (I) is stabilized, and a manufacturing method for such a solid product in the form of a tablet, a powder, granules, or a capsule in which the compound is stabilized, the present inventors achieved the object, and thus completed the present invention.

Solution to Problem

That is, as described below, the present invention is directed to a solid composition for medical use in which Compound (I) represented by the following structural formula is stabilized:

[Chem. 2]

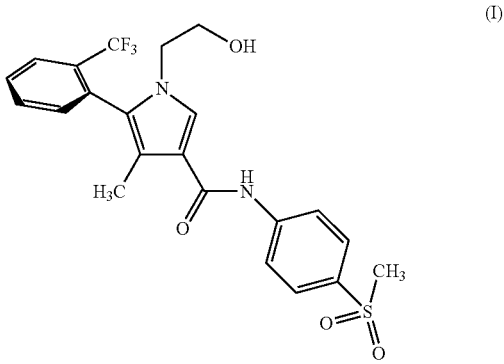

(I)

and a manufacturing method for the solid composition for medical use in which the compound is stabilized, further, a solid product in the form of a tablet, a powder, granules, or a capsule in which Compound (I) is stabilized, and a manufacturing method for such a solid product in the form of a tablet, a powder, granules, or a capsule in which the compound is stabilized.

Preferred embodiments of the present invention are as shown below:

(1) a solid composition for medical use, characterized by containing (S)-1-(2-hydroxyethyl)-4-methyl-N-[4-(methylsulfonyl)phenyl ]-5-[2-(trifluoromethyl)phenyl]-1H-pyrrole-3-carboxamide which is a compound having the following formula (I):

[Chem. 3]

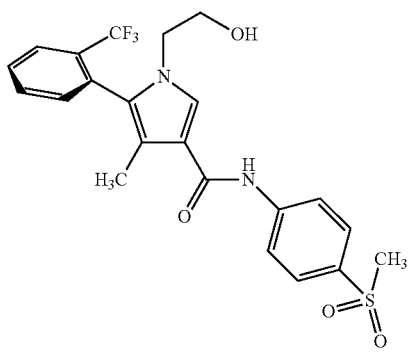

(I)

and lactose hydrate having an average particle diameter in the range of 5 to 50 μm, (2) a solid composition for medical use, characterized in that a decrease in dissolution of (S)-1-(2-hydroxyethyl)-4-methyl-N-[4-(methylsulfonyl)phenyl]-5-[2-(trifluoromethyl)phenyl]-1H-pyrrole-3-carboxamide is prevented by mixing (S)-1-(2-hydroxyethyl)-4-methyl-N-[4-(methylsulfonyl)phenyl]-5-[2-(trifluoromethyl)phenyl]-1H-pyrrole-3-carboxamide with lactose hydrate having an average particle diameter in the range of 5 to 50 μm and allowing the compounds to exist therein, (2-1) the solid composition for medical use described in the above (2), wherein in the dissolution test method (paddle method) according to The Japanese Pharmacopoeia 16th edition, a decrease in dissolution at a testing time of 30 minutes is prevented, (2-2) the solid composition for medical use described in the above (2), wherein in the dissolution test method (paddle method) according to The Japanese Pharmacopoeia 16th edition, a decrease in dissolution at 30 minutes from the start of the test is prevented after a step (i) and a step (ii):

(i) performing storage for 2 days in an open condition of a brown bottle without a lid in an environment at 40° C. and 75% RH, (ii) firmly closing the lid of the brown bottle after performing storage in (i), and then performing storage for 1 week in an environment at 60° C. without controlling the humidity, (3) the solid composition for medical use described in the above (1) or (2), wherein the lactose hydrate is lactose hydrate having an average particle diameter in the range of 15 to 50 μm, (4) the solid composition for medical use described in the above (1) or (2), wherein the lactose hydrate is lactose hydrate having an average particle diameter in the range of 15 to 40 μm, (5) a solid composition for medical use, characterized in that a delay in disintegration time is prevented by mixing (S)-1-(2-hydroxyethyl)-4-methyl-N-[4-(methylsulfonyl)phenyl]-5-[2-(trifluoromethyl)phenyl]-1H-pyrrole-3-carboxamide with lactose hydrate having an average particle diameter in the range of 5 to 50 μm and allowing the compounds to exist therein, (5-1) a solid composition for medical use in which a decrease in dissolution is prevented, characterized in that a delay in disintegration time is prevented by mixing (S)-1-(2-hydroxyethyl)-4-methyl-N-[4-(methylsulfonyl)phenyl]-5-[2-(trifluoromethyl)phenyl]-1H-pyrrole-3-carboxamide with lactose hydrate having an average particle diameter in the range of 5 to 50 μm and allowing the compounds to exist therein, (5-2) the solid composition for medical use described in any one selected from the above (1) to (5-1), further containing low-substituted hydroxypropyl cellulose and hydroxypropyl cellulose, (5-3) the solid composition for medical use described in any one selected from the above (1) to (5-2), further containing magnesium stearate, (5-4) the solid composition for medical use described in any one selected from the above (1) to (5-3), in which stability is improved by further mixing a coloring agent and allowing the agent to exist therein or by allowing a coloring agent to exist in a coating portion, (6) the solid composition for medical use described in the above (5), wherein the disintegration time is within 10 minutes, (7) the solid composition for medical use described in any one selected from the above (1) to (6), wherein the solid composition for medical use is a tablet, (8) a production method for a solid composition for medical use, including a step of mixing (S)-1-(2-hydroxyethyl)-4-methyl-N-[4-(methylsulfonyl)phenyl]-5-[2-(trifluoromethyl)phenyl]-1H-pyrrole-3-carboxamide with an additive including lactose hydrate having an average particle diameter in the range of 5 to 50 μm, (8-1) the production method described in the above (8), which is a manufacturing method for a solid composition for medical use, wherein a decrease in dissolution is prevented by including a step of mixing (S)-1-(2-hydroxyethyl)-4-methyl-N-[4-(methylsulfonyl)phenyl]-5-[2-(trifluoromethyl)phenyl]-1H-pyrrole-3-carboxamide with an additive including lactose hydrate having an average particle diameter in the range of 5 to 50 μm, (8-2) the manufacturing method described in the above (8), which is a manufacturing method for a solid composition for medical use, wherein a delay in disintegration time is prevented by including a step of mixing (S)-1-(2-hydroxyethyl)-4-methyl-N-[4-(methylsulfonyl)phenyl]-5-[2-(trifluoromethyl)phenyl]-1H-pyrrole-3-carboxamide with an additive including lactose hydrate having an average particle diameter in the range of 5 to 50 μm, (9) the manufacturing method described in the above (8), including:

a step of granulating (S)-1-(2-hydroxyethyl)-4-methyl-N-[4-(methylsulfonyl)phenyl]-5-[2-(trifluoromethyl)phenyl]-1H-pyrrole-3-carboxamide, lactose hydrate having an average particle diameter in the range of 5 to 50 μm, low-substituted hydroxypropyl cellulose, hydroxypropyl cellulose, and a coloring agent by a wet process; and a step of performing compression by adding magnesium stearate, (9-1) the production method described in the above (9), further including a coating step,

(10) the manufacturing method described in the above (8), including:

a step of granulating (S)-1-(2-hydroxyethyl)-4-methyl-N-[4-(methylsulfonyl)phenyl]-5-[2-(trifluoromethyl)phenyl]-1H-pyrrole-3-carboxamide, lactose hydrate having an average particle diameter in the range of 5 to 50 μm, low-substituted hydroxypropyl cellulose, and hydroxypropyl cellulose by a wet process; and a step of performing compression by adding magnesium stearate and a coloring agent, (10-1) the manufacturing method described in the above (10), further including a coating step,

(11) the manufacturing method described in the above (8), including:

a step of granulating (S)-1-(2-hydroxyethyl)-4-methyl-N-[4-(methylsulfonyl)phenyl]-5-[2-(trifluoromethyl)phenyl]-1H-pyrrole-3-carboxamide, lactose hydrate having an average particle diameter in the range of 5 to 50 μm, low-substituted hydroxypropyl cellulose, and hydroxypropyl cellulose by a wet process;

a step of performing compression by adding magnesium stearate, and a coating step using a coating agent containing a coloring agent, and

(12) the manufacturing method described in the above (9) to (11), wherein the coloring agent is yellow ferric oxide and/or red ferric oxide.

Advantageous Effects of Invention

The present invention has a characteristic in that in order to obtain a solid composition for medical use in which Compound (I) is stabilized, various difficulties were overcome, and in the end, the solid composition for medical use in which the compound is stabilized could be obtained.

According to the present invention, it becomes possible to prepare a solid composition for medical use in which Compound (I) is stabilized, and further, it becomes possible to provide a solid product in the form of a tablet, a powder, granules, or a capsule in which Compound (I) is stabilized, and to manufacture such a solid product in the form of a tablet, a powder, granules, or a capsule in which the compound is stabilized.

DESCRIPTION OF EMBODIMENTS

The lactose hydrate to be used in the present invention is not particularly limited as long as it can be used as an additive and has an average particle diameter in the range of 5 to 50 μm. For example, Lactochem® Powder, Lactochem® Fine Powder, Lactochem® Extra Fine Powder, Pharmatose® 450M, and Lactohale® 201 of DFE Pharma are preferably used.

The "average particle diameter" as used herein refers to a particle diameter when the integrated value reaches 50% in a particle size distribution obtained by a sieving device (for example, model "ATM sonic sifter" manufactured by ATM Corporation, or the like).

The solid preparation of the present invention may further contain an appropriate pharmacologically acceptable additive such as an excipient other than lactose hydrate, a lubricant, a binder, an emulsifier, a stabilizer, a corrigent, and/or a disintegrant as needed.

Examples of the "excipient" to be used include organic excipients including sugar derivatives such as lactose, lactose hydrate, white soft sugar, glucose, mannitol, and sorbitol; starch derivatives such as corn starch, potato starch, pregelatinized starch, and dextrin; cellulose derivatives such as crystalline cellulose; gum Arabic; dextran; and pullulan; and inorganic excipients including silicate derivatives such as light anhydrous silicic acid, synthetic aluminum silicate, calcium silicate, and magnesium metasilicate aluminate; phosphates such as calcium hydrogen phosphate; carbonates such as calcium carbonate; and sulfates such as calcium sulfate. The excipient is preferably one or more excipients selected from cellulose derivatives and sugar derivatives, more preferably one or more excipients selected from lactose, lactose hydrate, other crystals of mannitol, and crystalline cellulose, and most preferably, lactose hydrate.

Examples of the "lubricant" to be used include stearic acid; stearic acid metal salts such as calcium stearate and magnesium stearate; talc; colloidal silica; waxes such as beeswax and spermaceti; boric acid; adipic acid; sulfates such as sodium sulfate; glycol; fumaric acid; sodium stearyl fumarate; sucrose fatty acid esters; sodium benzoate; D,L-leucine; lauryl sulfates such as sodium lauryl sulfate and magnesium lauryl sulfate; silicates such as anhydrous silicic acid and silicate hydrate; and the above-mentioned starch derivatives. The lubricant is preferably a stearic acid metal salt.

Examples of the "binder" to be used include hydroxypropyl cellulose, hypromellose, polyvinylpyrrolidone, polyethylene glycol, and compounds similar to the above-mentioned excipients. The binder is preferably hydroxypropyl cellulose or hypromellose.

Examples of the "emulsifier" to be used include colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ethers, polyoxyethylene sorbitan fatty acid esters, and sucrose fatty acid esters.

Examples of the "stabilizer" to be used include p-hydroxybenzoate esters such as methyl paraben and propyl paraben; alcohols such as chlorobutanol, benzyl alcohol, and phenyl ethyl alcohol; benzalkonium chloride; phenols such as phenol and cresol; thimerosal; dehydroacetic acid; and sorbic acid.

Examples of the "corrigent" to be used include sweeteners such as sodium saccharin and aspartame; acidulants such as citric acid, malic acid, and tartaric acid; and flavors such as menthol, lemon, and orange.

Examples of the "disintegrant" to be used include cellulose derivatives such as low-substituted hydroxypropyl cellulose, carboxymethyl cellulose, calcium carboxymethyl cellulose, and internally crosslinked sodium carboxymethyl cellulose; cross-linked polyvinylpyrrolidone; and chemically modified starches and celluloses such as carboxymethyl starch and sodium carboxymethyl starch.

The blending amount of the compound having the above formula (I) or a pharmacologically acceptable salt thereof in the solid product is not particularly limited, however, it is preferably blended in an amount of, for example, 0.1 to 10.0% by weight (preferably 0.1 to 5.0% by weight) with respect to the total weight of the solid product.

Further, the blending amount of the additive in the total amount of the solid product is not particularly limited, however, for example, with respect to the total weight of the solid product, it is preferred to blend the excipient also including lactose hydrate in an amount of 10.0 to 93.5% by weight (preferably 44.0 to 90.0% by weight), the lubricant in an amount of 0.5 to 5.0% by weight (preferably 0.5 to 3.0% by weight), the binder in an amount of 0.0 to 15.0% by weight (preferably 1.0 to 5.0% by weight), and the disintegrant in an amount of 2.5 to 40.0% by weight (preferably 5.0 to 30.0% by weight).

The solid product of the present invention can be, for example, a tablet (including a sublingual tablet and an orally disintegrating tablet), a capsule (including a soft capsule and a microcapsule), granules, fine granules, a powder, a pill, a chewable agent, a troche, or the like, and is preferably a powder, fine granules, granules, a capsule, or a tablet, and most preferably a tablet.

The solid product of the present invention is obtained as a powder, granules, surface-coated granules, a capsule, a tablet, or a surface-coated tablet by sequentially performing the following procedures:

(1) adding an excipient which is a stabilizer and a disintegrant or the like, and further an auxiliary agent (a lubricant or the like) required for formulation to a powder of Compound (I) which is an active ingredient, and (2) a capsule filling step of compression filling the obtained granular powder by a capsule filling machine, or a tableting step of compressing the obtained granular powder by a tableting machine, and then, according to need, a coating step of coating the surface of the obtained granular powder, granules, or tablet.

Examples of the manufacturing method for the solid product include (1) a direct compression method in which an active ingredient and an additive are mixed and the resulting mixture is directly compression by a tableting machine, (2) a semi-direct compression method in which an additive is formed into granules, and an active ingredient is mixed with the granules, and then, the resulting mixture is compression-molded, (3) a dry granule compression method in which an active ingredient and an additive are granulated into granules by a dry process, and thereafter a lubricant or the like is added thereto, and the resulting mixture is compressed, and (4) a wet granule compression method in which an active ingredient and an additive are granulated into granules by a wet process, and thereafter a lubricant or the like is added thereto, and the resulting mixture is compressed. Further, as the granulation method, a fluidized bed granulation method, a high-shear granulation method, a melting granulation method, or the like can be used. In the present invention, a method in which an active ingredient and an additive are granulated into granules by a wet process, and thereafter a lubricant or the like is added thereto, and the resulting mixture is compressed, whereby a tablet is prepared is preferred.

For example, a manufacturing method for a tablet of the present invention is as described below.

Compound (I) which is the active ingredient is milled, and the particle diameter is sized, followed by granulation into granules along with an excipient, a binder, and/or a disintegrant by a wet process. Thereafter, the resulting granules are screened by a rotating screen machine, and then, a lubricant is added thereto, followed by further mixing, and then tableting the resulting mixture by a tableting machine, whereby a tablet is obtained.

Coating is performed using, for example, a film coating device, and as a film coating base agent, for example, a sugar coating base agent, a water-soluble film coating base agent, an enteric film coating base agent, a controlled-release film coating base agent, or the like can be used.

As the sugar coating base agent, white soft sugar is used, and further, it is also possible to use one type or two or more types in combination selected from talc, precipitated calcium carbonate, calcium phosphate, calcium sulfate, gelatin, gum Arabic, polyvinylpyrrolidone, pullulan, and the like.

Examples of the water-soluble film coating base agent include cellulose derivatives such as hydroxypropyl cellulose, hypromellose, hydroxyethyl cellulose, methylhydroxyethyl cellulose, and sodium carboxymethyl cellulose; synthetic polymers such as polyvinylacetal diethylaminoacetate, aminoalkylmethacrylate copolymers, and polyvinylpyrrolidone; and polysaccharides such as pullulan.

Examples of the enteric film coating base agent include cellulose derivatives such as hydroxypropylmethyl cellulose phthalate, hydroxypropylmethyl cellulose acetate succinate, carboxymethylethyl cellulose, and cellulose acetate phthalate; acrylic acid derivatives such as (meth)acrylic acid copolymer L, (meth)acrylic acid copolymer LD, and (meth)acrylic acid copolymer S; and natural substances such as shellac.

Examples of the controlled-release film coating base agent include cellulose derivatives such as ethyl cellulose; and acrylic acid derivatives such as aminoalkyl methacrylate copolymer RS or an ethyl acrylate-methyl methacrylate copolymer emulsion.

Two or more types of the above-mentioned coating base agents may also be mixed at an appropriate ratio and used. Further, the coating base agent may contain an appropriate pharmacologically acceptable additive such as a plasticizer, an excipient, a lubricant, a masking agent, a coloring agent, and/or a preservative as needed.

The type of the plasticizer which can be used in the present invention is not particularly limited, and can be appropriately selected by a person skilled in the art. Examples of such a plasticizer include propylene glycol, polyethylene glycol, polypropylene glycol, glycerin and sorbitol, glycerin triacetate, diethyl phthalate and triethyl citrate, lauric acid, sucrose, dextrose, sorbitol, triacetin, acetyltriethyl citrate, triethyl citrate, tributyl citrate, and acetyltributyl citrate.

Examples of the masking agent which can be used in the present invention include titanium oxide.

Examples of the coloring agent which can be used in the present invention include red ferric oxide, yellow ferric oxide, black iron oxide, titanium oxide, blue No. 1 (Brilliant Blue FCF), blue No. 2 (Indigo carmine), red No. 3 (Erythrosine), yellow No. 4 (Tartrazine), and yellow No. 5 (Sunset yellow FCF).

The coloring agent is preferably red ferric oxide, yellow ferric oxide, or black iron oxide, more preferably, red ferric oxide or yellow ferric oxide.

As for the content of the coloring agent to be used in the present invention, in the case where the coloring agent is included in an uncoated tablet, it is desired to blend the coloring agent in an amount of preferably 0.01 to 1% by weight (more preferably 0.02% or more to 0.1% by weight) with respect to the total weight of the uncoated tablet, and in the case where the coloring agent is included in a film coating component, it is desired to blend the coloring agent in an amount of preferably 0.003 to 0.1% by weight (more preferably 0.01% or more to 0.1% by weight) with respect to the total weight of the uncoated tablet.

Examples of the preservative which can be used in the present invention include paraben.

The dose of the compound having the above formula (I) or a pharmacologically acceptable salt thereof which is the active ingredient of the solid product of the present invention can vary depending on various conditions such as the efficacy of the active ingredient, the symptoms, age, or body weight of a patient, etc. In the case of oral administration, each can be generally administered to an adult at a daily dose of 0.010 mg (preferably 0.625 mg) as a lower limit and 100.0 mg (preferably 30.0 mg) as an upper limit.

(Production Method for Solid Preparation)

Next, the present invention will be described in further detail with reference to Examples or the like, however, the following Examples are for illustrative purposes only, and the present invention is not to be construed as being limited to these Examples.

EXAMPLES (Example 1) Particle Diameter of Lactose Hydrate and Stability of Product (1-1) Manufacturing Method for Tablet With respect to each lactose hydrate shown in Table 1, Compound (I), lactose hydrate, low-substituted hydroxypropyl cellulose (LH-21, Shin-Etsu Chemical), hydroxypropyl cellulose (HPC-L, Nippon Soda), and yellow ferric oxide (Kishi Kasei) were weighed at a blending ratio according to the composition shown in Table 2, and put in a high-shear agitation granulator (VG-5 or VG-10, Powrex) along with purified water, and kneaded for 3 minutes by setting the blade rotation speed to 280 or 250 rpm, whereby granules were obtained. These granules were dried by a fluid bed dryer (NFLO-2, Powrex or FLO-5M, Freund Corporation) until the product temperature reached 60° C. Thereafter, the granules were screened at 2200 pm using Comil (QC-197 or QC-194S, φ 1.143 mm, QUADRO), whereby screened granules were obtained. The screened granules and magnesium stearate were put in a V-type mixer (2 L) such that the mass mixing ratio was 99:1, and mixed at a rotation speed of 39 rpm for 5 minutes. The mixture was compressed using a tableting machine (Correct 18HUK, Kikusui Seisakusho) by setting the tablet weight to 200 mg and the tableting pressure to 10 kN, whereby an uncoated tablet with a diameter of 8.0 mm was obtained. The obtained uncoated tablet was coated with a film using a coating machine (Hi-Coater Labo 30, Freund Corporation) by setting the supply air temperature to 75° C. and the spraying speed to 3 g/min.

TABLE 1

| | Trade name | Average particle diameter (μm)* | High-shear agitation granulator | Fluid bed dryer | Comil |
|---|---|---|---|---|---|
| Lactose hydrate (1) | Pharmatose ® 450M (DFE Pharma) | 15 | VG-10 (blade rotation speed: 250 rpm) | NFLO-2 | QC-194S |
| Lactose hydrate (2) | Lactochem ® Fine Powder (DFE Pharma) | 40 | VG-10 (blade rotation speed: 250 rpm) | NFLO-2 | QC-194S |
| Lactose hydrate (3) | Dilactose ® S (Freund Corporation) | 94 | VG-10 (blade rotation speed: 250 rpm) | NFLO-2 | QC-194S |
| Lactose hydrate (4) | Dilactose ® R (Freund Corporation) | 171 | VG-5 (blade rotation speed: 280 rpm) | FLO-5M | QC-197 |

*average particle diameter of the lactose hydrate is the catalogue value obtained by measurement using a dry sieving method (ATM sonic sifter, ATM Corporation).

TABLE 2

| | Composition (mg/tablet) | | | | |
|---|---|---|---|---|---|
| Components | Tablet a | Tablet b | Tablet c | Tablet d | Tablet e |
| Compound (I) | 0.25 | 5.00 | 0.25 | 0.25 | 0.25 |
| Lactose hydrate (type) | (1) 161.75 | (1) 156.80 | (2) 161.75 | (3) 161.75 | (4) 161.75 |
| Low-substituted hydroxypropyl cellulose (LH-21, Shin-Etsu Chemical) | 30.00 | 30.00 | 30.00 | 30.00 | 30.00 |
| Hydroxypropyl cellulose (HPC-L, Nippon Soda) | 6.00 | 6.00 | 6.00 | 6.00 | 6.00 |
| Yellow ferric oxide (Kishi Kasei) | — | 0.20 | — | — | — |
| Magnesium stearate (Mallinckrodt) | 2.00 | 2.00 | 2.00 | 2.00 | 2.00 |
| Total weight of uncoated tablet | 200.00 | 200.0 | 200.00 | 200.00 | 200.00 |
| [Coating agent] | | | | | |
| OPADRY-OY-S 9607 (Colorcon) (hypromellose) (titanium oxide) (talc) | 9.90 (7.10) (1.40) (1.40) | — | 9.90 (7.10) (1.40) (1.40) | 9.90 (7.10) (1.40) (1.40) | 9.90 (7.10) (1.40) (1.40) |
| [Coloring agent] | | | | | |
| Yellow ferric oxide (Kishi Kasei) | 0.10 | — | 0.10 | 0.10 | 0.10 |
| Total weight of film-coated tablet | 210.00 | — | 210.00 | 210.00 | 210.00 |

(1-2) Evaluation Method and Results

With respect to the tablets (tablets a to e using each of the lactose hydrates 1 to 4) manufactured in Example (1-1), a disintegration test and a dissolution test were performed so as to compare tablets which were subjected to a storage process (storage A) under the following storage conditions that accelerate degradation of tablets (subjected to storage A) and tablets which were not subjected to storage A (control).

Storage A: A brown bottle in which a tablet is placed is stored for 2 days in an open condition without a lid in an environment at 40° C. and 75% RH, and thereafter, the lid of the brown bottle is closed, and then the bottle is stored for 1 week in an environment at 60° C. without controlling the humidity.

The dissolution test was performed in accordance with the dissolution test method (paddle method, 50 rpm) according to The Japanese Pharmacopoeia 16th edition, and evaluation was performed using 900 mL of an aqueous solution of 0.1% polysorbate 80 (TW-0120V, manufactured by Kao Corporation) as test solution. Further, the disintegration test was performed in accordance with the disintegration test method according to The Japanese Pharmacopoeia 16th edition, and evaluation was performed without using a disk.

The results are shown in Table 3.

(Example 2) Stability of Product by Addition of Color Agent (2-1) Manufacturing Method for Tablet Compound (I), lactose hydrate (Pharmatose 450M, DFE Pharma), low-substituted hydroxypropyl cellulose (LH-21, Shin-Etsu Chemical), hydroxypropyl cellulose (HPC-L, Nippon Soda), and yellow ferric oxide (Kishi Kasei) were weighed at a blending ratio according to the composition shown in Table 4, and put in a high-shear agitation granulator (VG-10, Powrex) along with purified water, and kneaded for 3 minutes by setting the blade rotation speed to 250 rpm, whereby granules were obtained. These granules were dried by a fluid bed dryer (FLO-5M, Freund Corporation) until the product temperature reached 60° C. Thereafter, the granules were screened at 2200 rpm using Comil (QC-194S, φ 1.143 mm, QUADRO), whereby screened granules were obtained. The screened granules and magnesium stearate were put in a V-type mixer (5 L) so that the mass mixing ratio was 99:1, and mixed at a rotation speed of 34 rpm for 5 minutes. The mixture was compressed using a tableting machine (Correct 18HUK, Kikusui Seisakusho) by setting the tablet weight to 200 mg and the tableting pressure to 10 kN, whereby an uncoated tablet with a diameter of 8.0 mm was obtained. The obtained uncoated tablet was coated with a film using a coating machine (Driacouter 200, Freund Corporation) by setting the supply air temperature to 75° C. and the spraying speed to 3 g/min.

TABLE 3

| | | Tablet a | Tablet b | Tablet c | Tablet d | Tablet e |
|---|---|---|---|---|---|---|
| Lactose hydrate type | | Lactose hydrate 1 | Lactose hydrate 1 | Lactose hydrate 2 | Lactose hydrate 3 | Lactose hydrate 4 |
| Average particle diameter* | | 15 | 15 | 40 | 94 | 171 |
| Storage conditions for Tablet | | control / subjected to storage A | control / subjected to storage A | control / subjected to storage A | control / subjected to storage A | control / subjected to storage A |
| Average disintegration time (min) | | 5 / 9 | 2 / 3 | 5 / 7 | 12 / 27 | 9 / 25 |
| Average dissolution ratio (%) | at 15 min | 87 / 82 | 78 / 77 | 90 / 86 | 73 / 21 | 84 / 26 |
| | at 30 min | 94 / 93 | 94 / 93 | 96 / 93 | 91 / 59 | 92 / 71 |

*average particle diameter of the lactose hydrate is the catalogue value obtained by measurement using a dry sieving method (ATM sonic sifter, ATM Corporation).

In the case of Tablet d and Tablet e using lactose hydrate 3 or lactose hydrate 4, each having a larger average particle diameter, the disintegration time of the tablet having been subjected to storage A was delayed by 15 minutes and 16 minutes, respectively, from that of the control. On the other hand, in the case of Tablet a, Tablet b, and Tablet c using lactose hydrate 1 or lactose hydrate 2, each having a smaller average particle diameter, the delay of the disintegration time was only 4 minutes, X minute, and 2 minutes, respectively.

Further, also with respect to the dissolution ratio (at 15 min and 30 min) in the case of Tablet d and Tablet e, the dissolution ratio of the tablets having been subjected to storage A was decreased by 20% or more, however, in the case of Tablet a, Tablet b, and Tablet c, the dissolution ratio almost did not change.

Therefore, it was demonstrated that the formulation using lactose hydrate having a smaller average particle diameter has an extremely high effect of preventing a delay in dissolution accompanying a delay in disintegration as compared with the formulation using lactose hydrate having a larger average particle diameter.

TABLE 4

| | Composition (mg/tablet) | | | | |
|---|---|---|---|---|---|
| Components | Tablet a | Tablet f | Tablet g | Tablet h | Tablet i |
| Compound (I) | 0.25 | 0.25 | 0.25 | 0.25 | 0.25 |
| Lactose hydrate (Pharmatose 450M, DFE Pharma) | 161.75 | 159.75 | 160.75 | 161.55 | 161.75 |
| Low-substituted hydroxypropyl cellulose (LH-21, Shin-Etsu Chemical) | 30.00 | 30.00 | 30.00 | 30.00 | 30.00 |
| Hydroxypropyl cellulose (HPC-L, Nippon Soda) | 6.00 | 6.00 | 6.00 | 6.00 | 6.00 |
| Yellow ferric oxide (Kishi Kasei) | — | 2.00 | 1.00 | 0.20 | — |
| Magnesium stearate (Mallinckrodt) | 2.00 | 2.00 | 2.00 | 2.00 | 2.00 |
| Total weight of uncoated tablet | 200.00 | 200.00 | 200.00 | 200.00 | 200.00 |

TABLE 4-continued

| Components | Composition (mg/tablet) | | | | |
|---|---|---|---|---|---|
| | Tablet a | Tablet f | Tablet g | Tablet h | Tablet i |
| [Coating agent] | | | | | |
| OPADRY-OY-S 9607 (Colorcon) | 9.90 | — | — | — | — |
| (hypromellose) | (7.10) | | | | |
| (titanium oxide) | (1.40) | | | | |
| (talc) | (1.40) | | | | |
| [Coloring agent] | | | | | |
| Yellow ferric oxide (Kishi Kasei) | 0.10 | — | — | — | — |
| Total weight of film-coated tablet | 210.00 | — | — | — | — |

(2-2) Evaluation Method and Results

The tablets produced in (2-1) were left under open conditions at 25° C./60% RH/25 days (2000 Lux/hour), and thereafter, the amount of organic impurities was measured under the conditions shown in Table 5 using HPLC (1290 Infinity, Agilent).

TABLE 5

| | |
|---|---|
| Measurement wavelength | 287 nm |
| Column | YMC-Pack Pro C18 RS (4.6 mm ID × 100 mm, 3.0 μm, manufactured by YMC) |
| Column temperature | 40° C. |
| Mobile phase A | 0.01 mol/L phosphate buffer (pH 3.4)/acetonitrile mixed solution (16:9) |
| Mobile phase B | Acetonitrile |
| Analysis time | 40 min |
| Injection amount | 10 μL |
| Sample cooler temperature | Constant temperature around 25° C. |

The results are shown in Table 6 (an increased amount (%) from the initial value of all organic impurities).

It is found that in the case of the tablets (Tablet a, and Tablets f to h) in which yellow ferric oxide was used as the coloring agent in the coating agent or in the uncoated tablet component, the increased amount from the initial value of all organic impurities which are increased by light was very small and therefore the stability is excellent as compared with the tablet (Tablet i) in which the coloring agent was not used.

TABLE 6

| Conditions | Tablet a | Tablet f | Tablet g | Tablet h | Tablet i |
|---|---|---|---|---|---|
| 25° C./60% RH/25 days Open conditions Light exposure 1,200,000 Lux (2000 Lux/hour) | 0.36% | 0.17% | 0.25% | 0.44% | 1.96% |

The invention claimed is:

1. A solid composition comprising (S)-1-(2-hydroxyethyl)-4-methyl-N-[4-(methylsulfonyl)phenyl]-5-[2-(trifluoromethyl)phenyl]-1H-pyrrole-3-carboxamide which is a compound having the following formula (I):

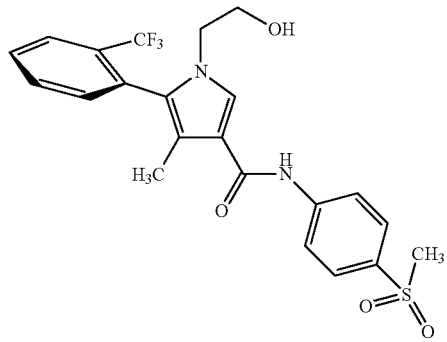

and lactose hydrate having an average particle diameter in the range of 5 to 50 μm.

2. The solid composition according to claim 1, wherein the lactose hydrate is lactose hydrate having an average particle diameter in the range of 15 to 50 μm.

3. The solid composition according to claim 1, wherein the lactose hydrate is lactose hydrate having an average particle diameter in the range of 15 to 40 μm.

4. The solid composition according to claim 1, wherein the disintegration time of the solid composition under physiological conditions is within 10 minutes as measured by a disintegration test specified in the Japanese Pharmacopoeia.

5. The solid composition according to claim 1, wherein the solid composition is a tablet.

6. A manufacturing method for a solid composition, comprising a step of mixing (S)-1-(2-hydroxyethyl)-4-methyl-N-[4-(methylsulfonyl)phenyl]-5-[2-(trifluoromethyl)phenyl]-1H-pyrrole-3-carboxamide with an additive including lactose hydrate having an average particle diameter in the range of 5 to 50 μm.

7. The manufacturing method according to claim 6, comprising:
a step of granulating (S)-1-(2-hydroxyethyl)-4-methyl-N-[4-(methylsulfonyl)phenyl]-5-[2-(trifluoromethyl)phenyl]-1H-pyrrole-3-carboxamide, lactose hydrate having an average particle diameter in the range of 5 to 50 μm, low-substituted hydroxypropyl cellulose, hydroxypropyl cellulose, and a coloring agent by a wet process; and
a step of performing compression by adding magnesium stearate.

8. The manufacturing method according to claim 7, wherein the coloring agent is yellow ferric oxide or red ferric oxide.

9. A method for increasing the rate of dissolution of a solid composition comprising (S)-1-(2-hydroxyethyl)-4-methyl-N-[4-(methylsulfonyl)phenyl]-5-[2-(trifluoromethyl)phenyl]-1H-pyrrole-3-carboxamide under physiological conditions, comprising mixing (S)-1-(2-hydroxyethyl)-4-methyl-N-[4-(methylsulfonyl)phenyl]-5-[2-(trifluoromethyl)phenyl]-1H-pyrrole-3-carboxamide with lactose hydrate having an average particle diameter in the range of 5 to 50 μm.

10. The method according to claim 9, wherein the lactose hydrate is lactose hydrate having an average particle diameter in the range of 15 to 50 μm.

11. The method according to claim 9, wherein the lactose hydrate is lactose hydrate having an average particle diameter in the range of 15 to 40 μm.

12. The method according to claim 9, wherein the disintegration time of the solid composition is within 10 minutes as measured by a disintegration test specified in the Japanese Pharmacopoeia.

13. The method according to claim 9, wherein the solid composition is a tablet.

14. A method for increasing the disintegration time of a solid composition comprising (S)-1-(2-hydroxyethyl)-4-methyl-N-[4-(methylsulfonyl)phenyl]-5-[2-(trifluoromethyl)phenyl]-1H-pyrrole-3-carboxamide under physiological conditions, comprising mixing (S)-1-(2-hydroxyethyl)-4-methyl-N-[4-(methylsulfonyl)phenyl]-5-[2-(trifluoromethyl)phenyl]-1H-pyrrole-3-carboxamide with lactose hydrate having an average particle diameter in the range of 5 to 50 μm.

15. The method according to claim 14, wherein the lactose hydrate is lactose hydrate having an average particle diameter in the range of 15 to 50 μm.

16. The method according to claim 14, wherein the lactose hydrate is lactose hydrate having an average particle diameter in the range of 15 to 40 μm.

17. The method according to claim 14, wherein the disintegration time of the solid composition is within 10 minutes as measured by a disintegration test specified in the Japanese Pharmacopoeia.

18. The method according to claim 14, wherein the solid composition is a tablet.

\* \* \* \* \*